United States Patent [19]
Lublin et al.

[11] 3,984,679
[45] Oct. 5, 1976

[54] COATING THICKNESS MONITOR FOR MULTIPLE LAYERS

[75] Inventors: Paul Lublin, Framingham; Donald Koffman, Winchester, both of Mass.

[73] Assignee: GTE Laboratories Incorporated, Waltham, Mass.

[22] Filed: Feb. 18, 1975

[21] Appl. No.: 550,496

[52] U.S. Cl. ............................... 250/272; 250/273
[51] Int. Cl.² .......................................... G01N 23/22
[58] Field of Search ............................ 250/272–279

[56] References Cited
UNITED STATES PATENTS

| | | | |
|---|---|---|---|
| 2,711,480 | 6/1955 | Friedman | 250/272 |
| 2,897,371 | 7/1959 | Hasler | 250/273 |
| 3,848,125 | 11/1974 | Utt et al | 250/272 |

*Primary Examiner*—Alfred E. Smith
*Assistant Examiner*—David K. Moore
*Attorney, Agent, or Firm*—Irving M. Kriegsman; Leslie J. Hart; Bernard L. Sweeney

[57] ABSTRACT

An apparatus for measuring the plating thickness of a thin gold coating on a substrate such as a sheet or thin wire is described. The gold plating thickness, which may range from one to about one hundred and fifty microinches, is measured with an X-ray analysis technique in real-time as the plating of a wire is in process. The gold plated wire is exposed to X-rays of a type and intensity selected to stimulate X-ray emission from both the gold plating and the substrate with energies which permit energy-dispersive analysis. A ratio between the X-ray energies attributable to the substrate and gold plating is employed to determine the thickness of the gold plating with a generally applicable calibration curve. The accurate and rapid gold plating thickness measurement enables the monitoring the regulation of the gold plating thickness with a feedback control in a highly accurate manner.

13 Claims, 6 Drawing Figures

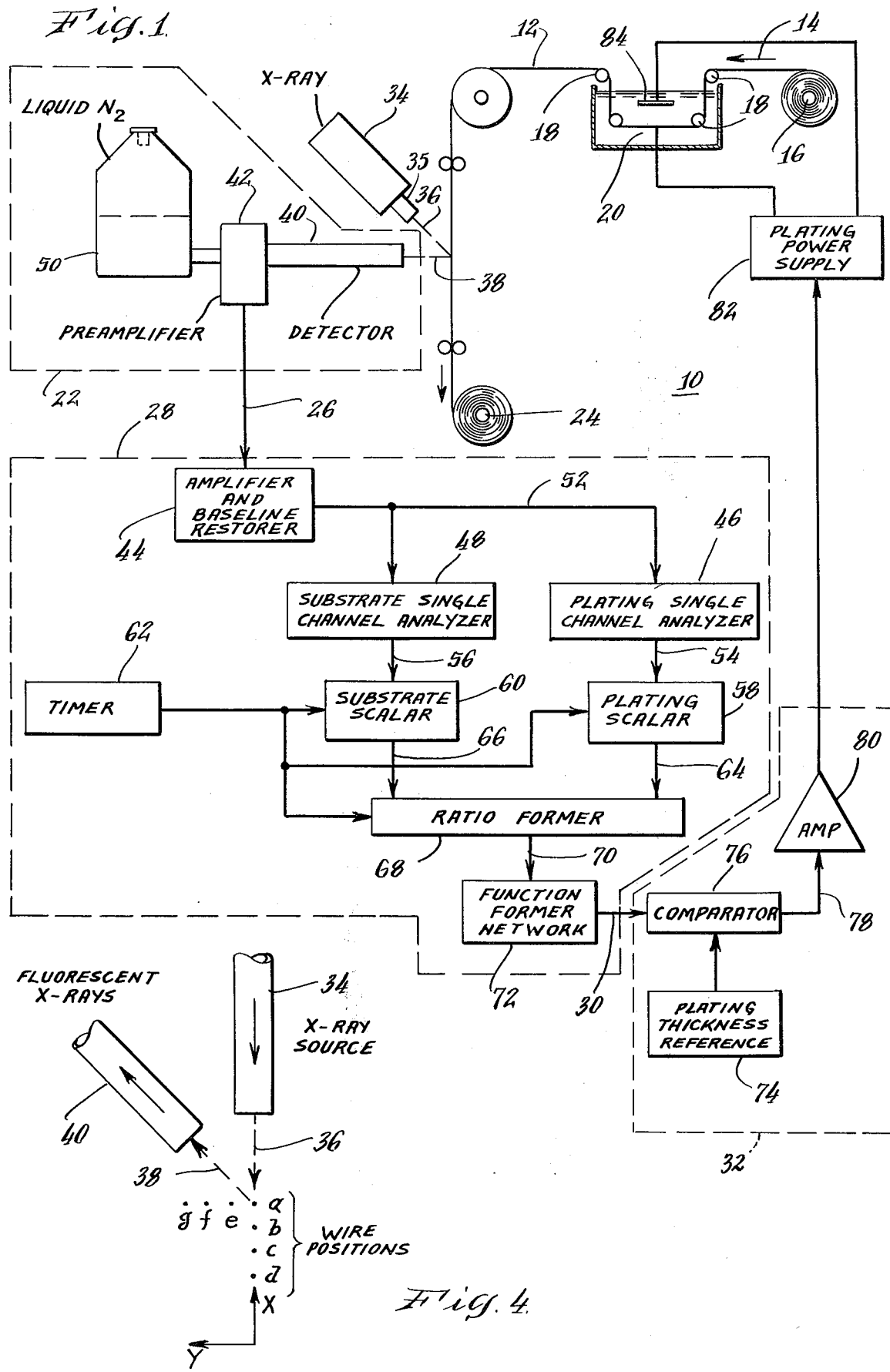

CALIBRATION CURVE X-RAY RATIO VS GOLD THICKNESS

COATING THICKNESS MONITOR FOR MULTIPLE LAYERS

BACKGROUND OF THE INVENTION

This invention relates to a method and apparatus for measuring the thickness of a coating. More specifically, this invention relates to a method and apparatus for continuously monitoring the thickness of a gold coating deposited onto a substrate.

In the manufacture of electrical conductors it is common to form a gold plating to enhance conductivity of the wire. The gold plating process involves passing a wire through an electroplating bath from which a thin coat of gold is plated onto the wire usually with a thickness of the order of from one to about 150 microinches.

The gold plating takes place while the wire is moved at a high speed, of the order of 100 to about 300 feet per minute, so that the thickness of the gold coat is difficult to control precisely. Since, for a particular application, a minimum thickness of the gold plating is needed, the actual plating process is set to deposit a gold coating whose thickness is substantially higher than that which is needed normally. In this manner, the gold coated wire can be assured of possessing the minimum acceptable amount of gold plating and fewer rejects occur. When one considers the scarcity and cost of gold, such a plating process is undesirably wasteful.

It would thus be advantageous to maintain control over the gold plating in such a manner that its maximum thickness can be held to within a few percent of a desired minimum thickness. However, such plating control is not readily obtainable with current practices of measuring the gold thickness on a wire, particularly when the wire is moving at a speed of the order of 100 feet per minute through the plating bath.

A variety of factors may affect the thickness of the plating, such as the plating bath solution concentration, the plating current and other well known factors. There are known methods for measuring thin coatings, such as a gold plating, of the order of a few microinches thickness. In one measurement method, a portion of a plated wire is selected and placed in an X-ray spectrometer for analysis. Such an approach involves an off-line measurement whereby the entire previously plated wire may be rejected if the measured gold thickness falls below an acceptable minimum level.

Another known plating thickness measuring technique involves a $\beta$-backscatter technique. This process involves the impingement of a beam of electrons on the plated wire whereby some electrons are absorbed and some are backscattered. For a given geometry and source, the intensity of the backscattered electrons provides an indication of the average atomic number of materials in the coating and substrate and the thickness of the coating. This method is inadequate when the atomic numbers of the plating material and the substrate material are close together. In addition, a relatively high background signal is generated regardless of sample thickness thereby limiting the ability of such a method to discriminate when the thickness signal is weak.

X-ray techniques for measuring the thickness of a gold plating are known and involve irradiating a sample with X-rays from an X-ray source or with radiation from an isotope source. The sample responds with the emission of X-rays which are characteristic of the material of the sample. Either the intensity of the substrate or plating X-ray lines or their ratio may then be a measure of thickness of the coating. The X-ray measuring techniques can be of the wavelength dispersive or energy dispersive kinds. Both techniques are well known and are described extensively in the literature.

In a conventional X-ray wavelength dispersive analysis of the thickness of the gold plating, there exists high sensitivity to the relative position of the wire to the detector as well as to variations in wire size. Such a sensitive response renders the wavelength dispersive X-ray analysis instrument less than fully desirable for monitoring and controlling the thickness of a coating deposited onto a substrate, such as gold plating on a wire, in an on-line application where it is desirable to perform the measurements in real-time on a moving sample. Furthermore, any change in the substrate or coating materials requires a physical change in the position of the X-ray detectors thereby limiting the versatility of such an apparatus.

SUMMARY OF THE INVENTION

In a method and an apparatus for measuring the thickness of a coating deposited on a substrate in accordance with the invention, one may control the thickness of the coating to a desirable tolerance during the coating process. As described with reference to a preferred embodiment in accordance with the invention, an energy dispersive analyzer, which is sensitive to X-ray radiation from a coated wire, is used to generate signals characteristic of the coating and the substrate. A ratio between the coating and substrate signals is formed and used to derive a thickness signal indicative of the thickness of the coating.

The thickness signal is generated in an accurate, reliable, rapid manner so that it can be conveniently employed to control the coating process through feedback. For example, the thickness signal may be compared with a signal representative of the desired coating thickness and the measured error may then be used to regulate the coating process to achieve the desired coating thickness.

The method and apparatus for measuring the thickness of a coating in the manner of the invention have an advantageous lack of sensitivity to variations in the position of the substrate material, such as a wire, with respect to the source of X-rays and the X-ray detector as well as to intensity variations from the X-ray source. A large variety of X-ray sources may be employed to achieve an optimization of the sensitivity of the apparatus for a wide range of coating and substrate materials. The simultaneous detection and recording of the characteristic lines from the coating and substrate enable a rapid analysis for real-time coating process control. The apparatus provides a stable mechanical configuration which requires little alignment, yet provides a high resolution to separate characteristic X-rays from the coating and substrate.

In another embodiment of the invention, the method and apparatus are also capable of monitoring the thickness of an intermediate plating layer, such as where a copper substrate is first nickel plated before it is gold plated to improve adherence of the gold.

It is, therefore, an object of the invention to provide a method and apparatus for measuring the thickness of a coating on a substrate immediately after the coating process.

It is a second object of the invention to provide such a method and apparatus which are sufficiently insensitive to minor variations in position between the apparatus and sample and to variations in operational parameters of the apparatus to be practical for on-line use.

It is a further object of the invention to provide an accurate X-ray technique for measuring and controlling the thickness of a material plated onto a substrate, such as a gold flash coating on a wire or other substrate.

It is a still further object of the invention to provide a method and apparatus for measuring the thickness of a coating on a substrate with high precision to enable accurate coating process control for a reduction of waste material.

It is another object of the invention, to provide such a method and apparatus which can function in real-time.

Further objects, advantages, and features of the invention will be apparent from the following detailed description of the preferred embodiments taken together with the accompanying drawing.

BRIEF DESCRIPTION OF DRAWING

FIG. 1 is a schematic block diagram of a preferred embodiment of an apparatus according to the present invention for measuring and controlling the thickness of a coating material, such as a gold plating, on a wire;

FIG. 4 is a schematic representation of the relative positional changes used to obtain the curves in FIG. 3;

DETAILED DESCRIPTION OF THE PREFERRED EMBODIMENTS

Figure 3:
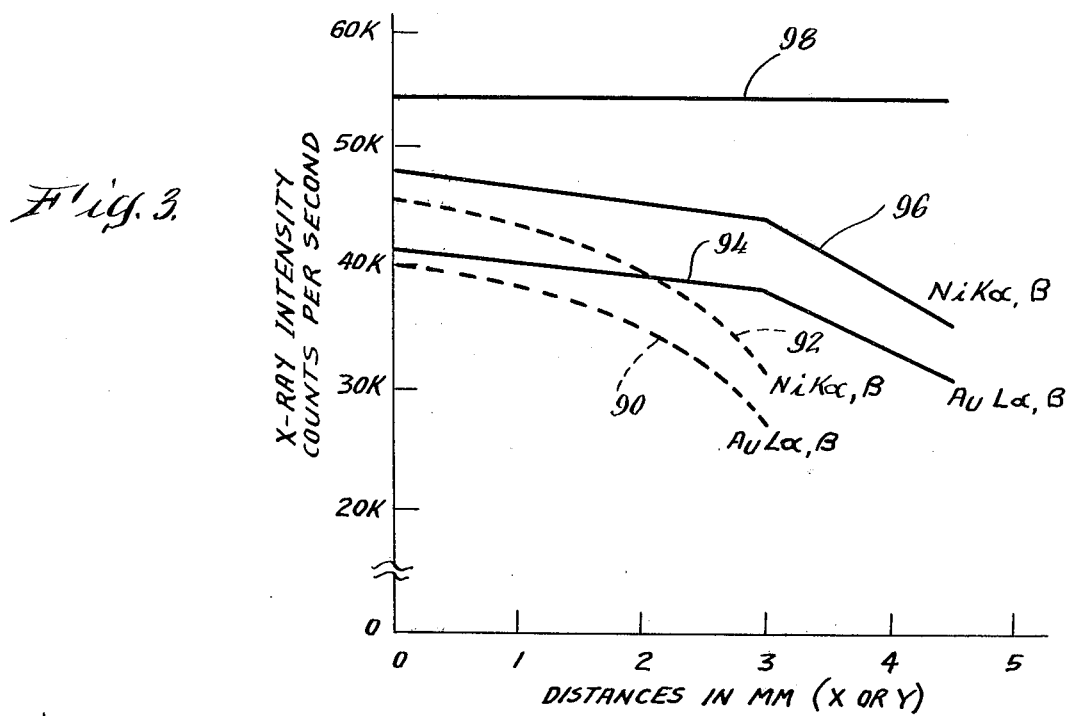
FIG. 3 is a plot showing curves of the sensitivity of the intensities of X-ray detections as a function of the position of the wire relative to the X-ray detector.

In referring to the various figures of the drawing hereinbelow, like reference numerals will be used to refer to identical parts of the apparatus.

With reference to FIG. 1, an apparatus 10 for measuring and controlling the thickness of a gold plating on a wire in accordance with the invention is shown. A copper wire strand 12 is shown being moved in the direction of an arrow 14 from a supply reel 16. The wire 12 is passed via suitable guide rollers 18 through a plating bath 20 and past an X-ray source 34 and an associated X-ray analysis spectrometer 22 to a take-up roller 24. An output signal on a line 26 of the X-ray spectrometer 22 is applied to a plating thickness measuring circuit 28 which generates a thickness signal on a line 30 indicative of the thickness of the plating on the wire 12. The thickness signal on the line 30 is applied to a control circuit 32 to regulate the thickness of the gold plating process in the bath 20 in accordance with a desired preselected coating thickness. In this manner, a real-time feedback control over the plating process is provided to regulate and maintain the desired gold thickness on the plated wire 12.

An X-ray detector 40 is responsive to the entire energy spectrum of the secondarily emitted X-ray beam 38 from the plated wire 12 and absorbs all of its incident X-ray energy. The detector output is amplified by a preamplifier 42 whose output on the line 26 in turn drives an amplifier 44. The output on a line 52 of the amplifier 44 is applied to a pair of single channel analyzers 46 and 48. The analyzers are set to respond respectively to characteristic X-ray energies for the coating, e.g., a gold plating, and the underlying wire substrate. Such analyzers are well known in the art and produce a series of pulses proportional in number to those X-rays attributed to the coating material energy band or the substrate material energy band.

In the preferred embodiment, the X-ray source 34 is an X-ray generator capable of supplying 50 KV and up to 50 Ma to a sealed water-cooled X-ray diffraction tube and may be selected to yield X-ray radiation which is particularly suited for causing enhanced X-ray fluorescence from the plated material, i.e., is close to the absorption edge. For the detection of a gold plating over a copper or nickel substrate, an X-ray target formed of molybdenum has been found to be effective. With a molybdenum target, there is sufficient X-ray energy to excite gold X-rays, i.e., the AuL spectra, with sufficient separation between the MoK radiation and the AuL$\alpha$ and AuL$\beta$ energy for accurate detection. In contrast, a tungsten target has been found to be relatively inefficient in exciting the AuL energies and the WL$\beta_1$ and WL$\lambda_1$ energies are difficult to separate from the gold X-ray signal. A collimator 35 is utilized at the output of the source 34 to reduce the background signal at the detector 40.

Any other radiant energy source which is capable of stimulating secondary X-rays to be emitted by the plating and substrate may be substituted for the X-ray source 34 within the purview of the invention. Radio isotopes are such a source. However, at present, the stimulated secondary X-ray flux from such isotopes achieved is too small for practical application in on-line apparatus.

The X-ray detector 40 may be as generally described with respect to solid state energy dispersive spectrometers. Such detectors are described in greater detail in *Energy Dispersion X-ray Analysis: X-ray and Electron Probe Analysis*, J. C. Russ Coordinator, American Society for Testing Materials, ASTM–485, May 1971. Preferably the detector is a Princeton Gamma Tech solid state intrinsic Germanium (or a lithium drifted silicon detector). Both the detector 40 and the associated preamplifier 42 are mounted in a vacuum cryostat cooled by a liquid nitrogen supply 50.

The solid state detector 40 requires a high electric field across a region of low conductivity. The intrinsic conductivity of either silicon or germanium is not sufficiently low at room temperature to prevent leakage current noise from dominating the detected photon signal. This problem may be circumvented effectively by lowering the temperature of the detector material to liquid nitrogen temperatures with the supply 50. The electric field and active volume of the detector are increased by employing the semiconductor junction with reverse bias and, in the case of silicon, by the addition of lithium compensation. The later compensation permits widening of the high field region by neutralization of the electrical activities in the depletion zone.

The liquid nitrogen cooling is desirable not only to reduce thermally created noise in the detector 40 and the first field-effect transistor in the preamplifier 42, but also to prevent lithium migration in a silicon detector. Since room temperature storage of lithium compensated silicon can result in small changes in the detector characteristics, an intrinsic germanium detector 40 is prefered to enable room temperature storage without degradation in performance. In such a case, liquid nitrogen is used only when the spectrometer 22 is placed in operation.

The free charge carriers (electron-hole pairs) generated by an X-ray photon move toward the collection electrodes under the influence of an applied electric field (not shown). In practice, a large bias is employed resulting in carrier velocity saturation. This and the lack of internal detector gain makes the collected charge relatively insensitive to variations in bias potential.

In order to achieve a low noise preamplifier 42, the latter employs field effect transistors operated at low temperatures. The preamplifer 42 is thus shown as being mounted close to the liquid nitrogen supply 50. Suitable electrical isolation and proper ground returns are employed to prevent low frequency noise interference within the preamplifier 42.

The main amplifier 44 provides sufficient amplification to enable energy band discrimination by the analyzers 46 and 48. The output on the line 52 of amplifier 44 is adjusted to provide pulses within the dynamic range typically (0 to 10 volts) of the analyzers 46 and 48. The design of the amplifier 44 is well known in the art of X-ray spectroscopy and thus need not be shown with greater detail herein. Preferably, the amplifier 44 provides d.c. baseline restoration and has sufficient response time to present accurately the amplified X-ray pulse signals to the pair of single channel analyzers 46 and 48. A 0.25 microsecond pulse shaping constant is desirable for obtaining high counting rates.

The analyzers 46 and 58 examine the X-ray intensity incident upon the detector 40 and are equipped with baseline and window width controls as are well known in the art to select particular energy bands of interest. A single channel analyzer, such as made by Tennelec Corporation of Oak Ridge, Tenn. model TC441, may be used. The outputs on lines 54 and 56 of the analyzers 46 and 48, respectively are pulses of very short duration and these are accumulated in a pair of scalars 58 and 60, associated with respective analyzers. The pulses are accumulated for a fixed time period controlled with a timer 62. In this manner, the pulse counts in the scalars 58 and 60, respectively, represent the intensities of the secondary X-rays emitted by the gold and substrate of the wire 12 in response to an incident X-ray beam 36.

In an alternate approach, counts representative of X-ray intensities can be obtained by accumulating a predetermined number of pulses. In such case, the time needed to achieve these counts can be used to indicate the X-ray intensities.

The outputs on lines 64 and 66 from the scalars 58 and 60, respectively, are in the form of counts for the selected time interval. The scalar outputs are applied to a circuit 68 for generating a ratio between the X-ray intensities attributable to the plating and substrate of the wire 12. Preferably, the relative ratio of the X-ray intensity of the gold to that of the substrate is formed. The ratio forming circuit 68 may be a rate multiplier or such other well known digital circuit for forming the desired ratio between digital counts.

The output on a line 70 from the ratio former circuit 68 is thereupon applied to a function former network 72 which produces a thickness signal indicative of the measured value of the ratio between the X-ray intensities. As can be seen from curve 73 in FIG. 2, the ratio of gold to substrate X-ray intensities bears a non-linear relationship with the thickness of the gold plating. The function former circuit 72, therefore, provides a corresponding non-linear correction so that a direct indication of the thickness of the gold plating appears on the output line 30.

The function former circuit 72 may be an analog circuit whose digital ratio input from the ratio former circuit 68 is converted to an analog value with a suitable digital to analog converter (not shown). A suitable number of non-linear diode signal-shaping networks can be employed to approximate the curve shown in FIG. 2. Such networks are well known in the art and need not be described with further detail.

With an analog thickness signal on the output line 30, a real-time control over the thickness of the gold plating is obtained conveniently. Thus, the control circuit 32 is shown to be provided with a reference signal source 74, whose amplitude signifies a desired gold plating thickness. A comparator 76 produces a thickness error signal on a line 78 indicative of the magnitude and direction of the difference between the measured thickness signal on the line 30 and the reference source 74. The error signal may then be amplified by an amplifier 80 and used to regulate the thickness of the gold plating in the bath 20 such that the error signal goes to a minimum level. Various well known control techniques may be applied to achieve the desired real-time plating thickness control once a reliable and accurate plating thickness error signal has been obtained.

The output of the amplifier 80 is shown coupled to a variable plating power supply 82 coupled between both a plating electrode 84 and the wire 12. This enables the regulation of the plating current and thus the thickness of the gold plating. It should be realized, however, that the plating thickness error signal may be used to control other plating process parameters to achieve the desired real-time feedback plating control. For example, one may seek plating bath temperature adjustments or plating solution concentration changes in response to the plating signals. Furthermore, if the process is another kind of process by which a coating is applied to a substrate, the error signal may be used to vary selected operational parameters to control coating thickness.

The total amount of X-ray flux, i.e., all secondary X-rays emitted from the wire 12, has been found to be a function of several factors. The power settings of the X-ray source 34 and the diameter of the wire 12 resulted in an increase in total X-ray flux for respective increases in power and wire diameter. Also, the variations in the distance between the wire 12 and the source 34 and the detector 40 strongly influence the X-ray flux as can be seen for curves 90, 92, 94 and 96 in FIG. 3. In addition, the total X-ray flux is reduced by decreases in the gold plating thickness. This decrease can be explained as a result of a decrease in the total volume of wire material which is excited by the source X-rays.

In order to keep the total X-ray flux within accurately measurable limits over a range of different thicknesses of the gold plating, the X-ray source 34 is set to yield a total secondary X-ray flux for a wire plated with more than about 40 microinches of gold to a predetermined level in the general vicinity of 70,000 counts per second. In this manner, the total secondary X-ray flux for an unplated wire 12 of the same diameter does not exceed a maximum level of about 100,000 counts per second. Above about 100,000 counts per second, the accuracy begins to deteriorate with present equipment. Thus, at the start of a gold plating monitoring process, the X-ray source 34 is set to yield the maximum level of total secondary X-ray flux as a function of the unplated wire diameter by positioning the unplated wire in the path of the primary X-ray beam 36. Alternatively, one may also adjust either or both of the wire 12 to-source 34 distance or the wire 12 to-detector 40 distance to achieve the desired level of total X-ray flux from the wire 12.

The marked sensitivity of the absolute pulse counts attributable to either the gold plating or the substrate to X-ray source changes, wire diameter variations, and the like renders these pulse counts by themselves difficult to use as a process control parameter. However, it has been found that a ratio of the pulse counts specifically attributable to the gold plating to the pulse counts specifically attributable to the wire substrate provides a parameter which is sufficiently stable for practical use in measuring the gold plating thickness.

FIG. 3 shows the variations in X-ray intensities from the substrate and the coating of the wire 12 as a function of the spacings of wire 12 from the source 34 and the detector 40. Thus, curve 90 shows a decrease in gold, $AuL\alpha,\beta$, intensity from 40K to 25K pulse counts as the wire 12 is moved a total of 3 mm in the direction of the Y axis (see FIG. 4, from point $a$ to points $e, f,$ and $g$ respectively). Similar variations can be noted for the substrate X-rays, $NiK\alpha, \beta$, in curve 92 when the wire is moved the same 3mm along the Y axis. When the wire is moved along the X axis (see FIG. 4, from point $a$ to points $b, c,$ and $d$ respectively), a distance of 4.5 mm, the gold plating and the nickel substrate X-ray intensities change as illustrated by the curves 94 and 96, respectively.

However, when a ratio of the gold plating X-ray intensity to the substrate X-ray intensity is plotted for the curves 90 and 92 or 94 and 96 as a function of the changes in wire position, an overlapping straight line curve 98 is obtained as shown in FIG. 3.

Although sufficiently precise positioning of the wire 12 relative to the source 34 and detector 40 can be maintained physically over small distances, the use of the X-ray intensity ratio as the process control parameter has further advantages as can be appreciated when other parameter variations in the plating process are examined. Thus, wire diameter variations and voltage or power fluctuations of the X-ray sources are effectively cancelled. In addition, the use of the X-ray intensity ratio provides enhanced sensitivity in the plating thickness measurement.

Figure 2:
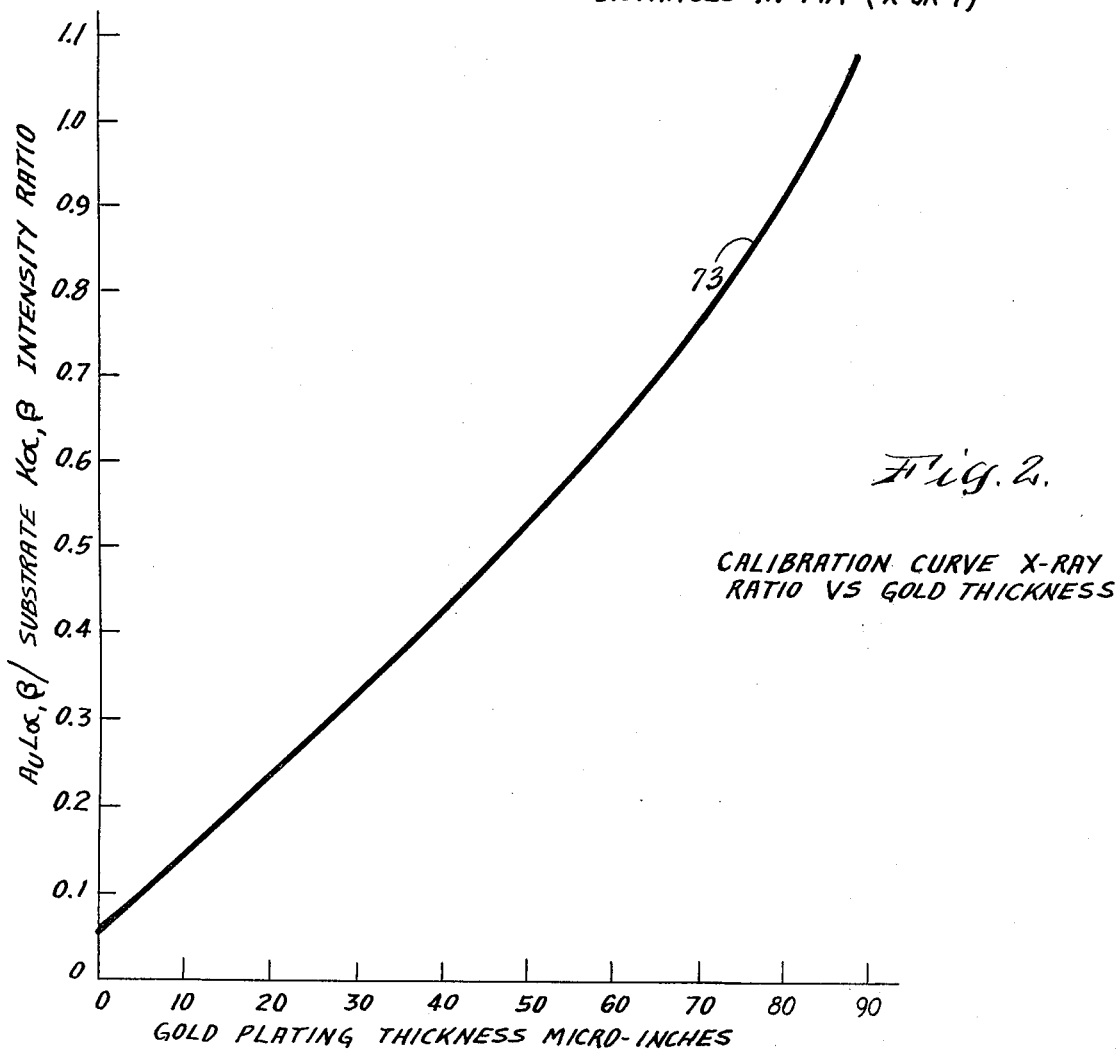
FIG. 2 is a plot of a calibration curve of the ratio of the X-ray intensities from a gold plating and its underlying substrate as a function of the thickness of the gold plating.

Referring now to FIG. 2, a ratio calibration curve 73 is obtained by plotting different X-ray intensity ratios for different wire samples as a function of the thickness of the gold plating. The gold plating thickness of the reference samples may be determined by dissolution of the measured plated wire using a well known atomic absorption method. The averaging effect involved in this method corresponds conveniently with the averaging effect obtained during a plating thickness measurement with the apparatus 10 while the wire 12 is moving.

The ratio calibration curve 73 shows a non-linear behavior of the measured X-ray intensity ratio as a function of the thickness of the gold plating. This can be explained on the following basis: as the gold plating thickness increases, the $AuL\alpha,\beta$ X-ray intensity increases and approaches a value corresponding to an infinitely thick gold plating. Simultaneously the substrate X-ray intensity decreases and approaches a small background value. Since the plating thickness range of interest centers about a level of 50 microinches of gold, the X-ray intensity ratio curve 73 is highly suitable for measuring the gold plating thickness in the one to one hundred microinch range.

The X-ray intensity calibration curve 73 has been found to be usable for a wide range of substrate materials such as DUMET, copper, nickel, and nickel plated DUMET wire having wide variations in nickel plating thickness. In addition, the same calibration curve 73 has been found to apply to wire diameters ranging from 0.008 inches to 0.40 inches. The advantage gained by this feature of the invention can be best appreciated when it is noted that if a wavelength dispersion technique is utilized a separate calibration curve is required for each combination of substrate and coating materials, relative sample to detector position, and different size of sample. Here only a single such curve is sufficient.

In order to take full advantage of the X-ray intensity ratio calibration curve 73, the plating single channel analyzer 46 has its baseline and pulse height window level set to accept two strong gold X-ray peaks for the $AuL\alpha$ and $AuL\beta$ energy lines. Further care is taken to insure that no substrate X-ray energy is allowed through the window of the analyzer 46.

The substrate channel analyzer 48 has its baseline and pulse height set so that all possible substrate X-ray energies are measured. Thus, copper X-rays, $CuK\alpha$, $CuK\beta$, for a copper or DUMET substrate and nickel X-rays, $NIK\alpha$, $NiK\beta$, for a nickel substrate are measured by the substrate analyzer 48. In this manner, X-rays from both the nickel and copper substrates for a nickel plated DUMET wire will be measured. Beryllium-copper substrates also may be measured. Similar baseline and pulse height setting combinations may be ascertained for other coating and substrate material combinations.

It should be noted that the $CuK\alpha$ X-ray radiation from a copper substrate in a nickel plated copper wire may produce secondary fluorescence $NiK\alpha$ X-rays from the nickel plating. Since all of the substrate X-ray energies are summed with the analyzer 48, the secondary fluorescence effect is accompanied by a loss in the $CuK\alpha$ X-rays which produced the secondary X-rays. Therefore, the net effect of such secondary X-ray fluoresence is very small.

The apparatus and method of this invention are further useful to measure the thickness of a layer underlying a surface gold coating such as occurs when a nickel layer is used to improve gold adherence to the substrate. The measurement of the thickness of such an underlying nickel layer can be employed, for example, in an on-line plating process to identify unacceptably thin nickel platings on wires.

Figure 5:
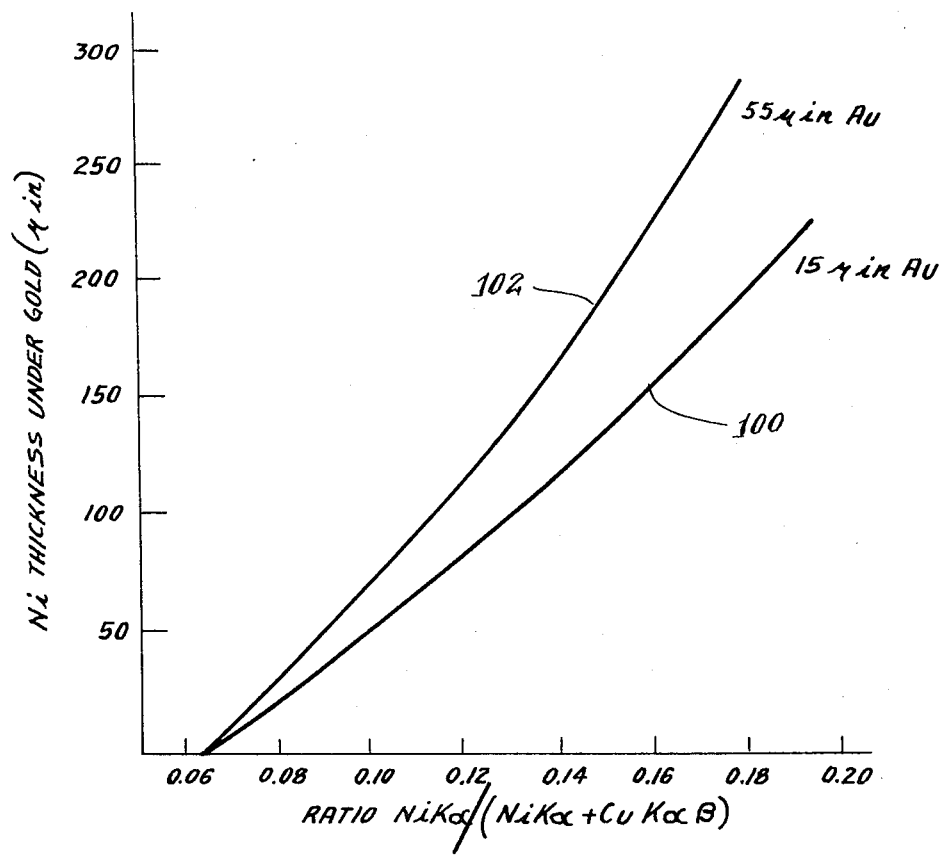
FIG. 5 is a plot of calibration curves for two thicknesses of gold of the ratio of X-ray intensities from an underlying nickel layer and its underlying substrate as a function of the thickness of the nickel layer which is useful for determining the thickness of the nickel plating layer.

With reference to FIG. 5, a pair of calibration curves 100 and 102 are shown and are applicable to a copper wire having a nickel layer over which a gold plating is formed. A ratio signal is produced with a network such as 28 (see FIG. 1) of the NiKα X-ray with respect to the sum of NiKα + CuKα,β X-rays. The thickness of the nickel plating may then be obtained as a function of the previously measured gold plating thickness by using either of the curves 100 or 102 or an interpolated value therefrom.

Figure 6:
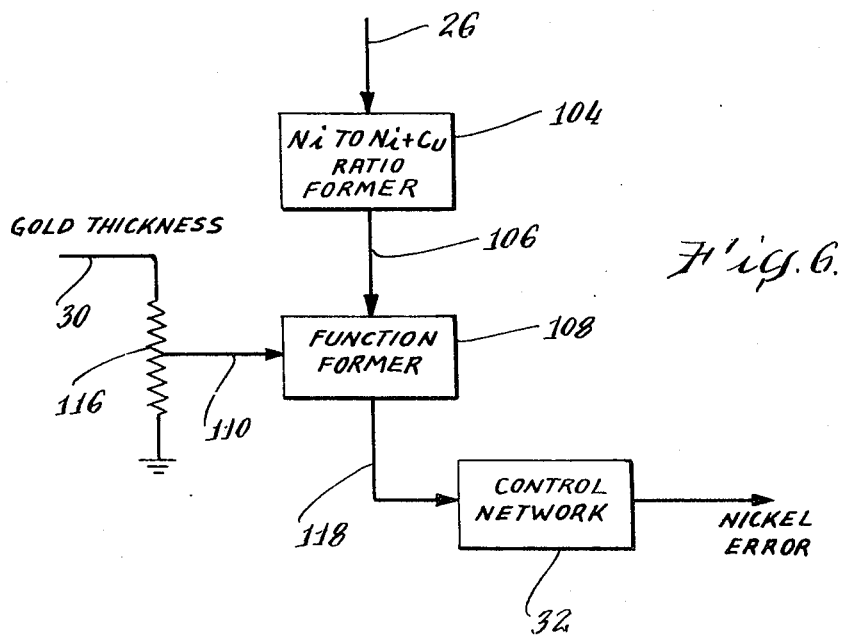
FIG. 6 is a block diagram for a network to measure automatically the thickness of the underlying nickel layer.

FIG. 6 shows a network for obtaining the nickel plating measurement with a previously measured gold thickness signal. The Ni to Ni + Cu ratio signal is obtained with a ratio former network 104 which includes a pair of single channel analyzers, such as 58 and 60 as previously described, but set to respond respectively to the nickel X-rays, NiKα, and the combination of nickel and the underlying copper substrate X-rays, CuKα, β. The outputs of the single channel analyzers are applied to a ratio former, such as at 68, to develop the ratio signal.

The ratio signal found on line 106 from the output of the ratio former 104 is applied to a function former circuit 108 whose response corresponds to the curves 100 and 102 of FIG. 5 depending upon an analog gold thickness signal 30 produced in the manner as previously described and applied to an input line 110 to the function former circuit 108. The function former circuit 108 is of the type whose output curve shape can be altered with an input signal on line 110 from the potentiometer 116 whose setting is related to the curves 100 and 102.

Slope and curve changing networks are generally well known in the art and thus need not be further explained. For purposes of explanation, the gold thickness signal 30 is shown applied across a potentiometer 116 to provide the function former network 108 with the proper input needed to obtain the correct underlying layer thickness signal on an output line 118.

The nickel thickness signal on line 118 may then be employed with a network, such as 32, to establish a control signal to regulate the thickness of the nickel plating or to provide other suitable indications as may be desirable in the particular application.

Although the foregoing description of the invention has been centered on the application of determining and/or controlling the thickness of a plating layer(s) on a wire, the application of the invention to samples having other geometries is included within the purview of that invention.

Having thus described a method and apparatus for measuring the thickness of a thin gold plating on a wire, the advantages of the invention can be appreciated. The measurement of the thickness of the gold plating may be obtained to a reliable accuracy of about one percent, or better, thus enabling for closer control of tolerances during the gold plating process. The invention may be applied to sheet and selected area plating as well as to different coating materials on different substrates with the various equipment parameters and calibration curves changed in the manner as taught herein. The functions of the circuits described and shown in FIG. 1 may be obtained also with a digital processor.

While there have been shown and described what are considered to be the presently preferred embodiments of the present invention, it will be obvious to those of ordinary skill in the art that various changes and modifications may be made therein without departing from the spirit of the invention as defined by the appended claims.

We claim:
1. An apparatus for measuring the thickness of a layer of a coating material deposited over a substrate material which is different from the coating material comprising:
   a source of a radiant energy which is directed onto the coated substrate, the radiant energy being capable of stimulating characteristic secondary X-rays from the coating material and the substrate material,
   an X-ray analysis spectrometer located to receive the characteristic secondary X-rays from the coating material and the substrate material simultaneously, the X-ray analysis spectrometer producing an output signal containing intensity information for a wide energy spectrum selected to include the characteristic secondary X-rays from the coating material and the substrate material,
   a coating thickness measuring circuit connected to the output of the X-ray analysis spectrometer which includes
   means for generating a signal which is indicative of the intensity of secondary X-rays received by the X-ray analysis spectrometer which are characteristic of the coating material, including
      a coating material energy dispersive single channel analyzer for generating X-ray counts of X-ray line energies associated exclusively with the coating material,
      a coating material scalar circuit which collects the X-ray counts from the coating material analyzer, and
      a timing circuit connected to the coating material scalar circuit to cause the scalar circuit to collect X-ray counts for a preselected period of time, the output signal from the scalar circuit being indicative of the intensity of the secondary X-rays characteristically associated with the coating material, means for generating a signal which is indicative of the intensity of secondary X-rays received by the X-ray analysis spectrometer which are characteristic of the substrate material, including:
      a substrate coating energy dispersive single channel analyzer for generating X-ray counts of X-ray line energies associated exclusively with the substrate material,
      a substrate material scalar circuit which collects the X-ray counts from the substrate material analyzer, and
      the timing circuit being connected to the substrate material scalar circuit to cause the scalar circuit to collect X-ray counts for a preselected period of time, the output signal from the scalar circuit being indicative of the intensity of the secondary X-rays characteristically associated with the substrate material,
   means responsive to the outputs of the timer and the scalar circuits for generating a signal which is a ratio of the two signals indicative of the secondary emission intensities, and
   means for generating, in response to the ratio signal, a signal which is indicative of the thickness of the layer of coating material.

2. An apparatus according to claim 1, wherein there are further included means for generating an error signal in response to the thickness signal which is indicative of any variation of the coating thickness from a predetermined level, and means for varying a coating process parameter in response to the error signal in a manner such that the coating thickness is altered in a direction which will cause the error signal to diminish.

3. An apparatus according to claim 2, wherein the means for generating an error signal includes a coating thickness reference circuit which supplies a reference signal indicative of the desired thickness of the coating material, and a comparator circuit which compares the coating thickness signal with the reference signal and generates the error signal.

4. An apparatus according to claim 1, wherein the means for generating a signal which is indicative of the thickness of the layer of coating material includes a function forming circuit selected to provide a nonlinear response in a predetermined manner to the ratio signal, the function forming circuit simulating a calibration curve of the thickness of the coating as a function of the ratio between emission energy intensities attributable to the substrate and the coating.

5. A method for measuring the thickness of a layer of a first coating material deposited over a substrate material which is different from the coating material and for measuring the thickness of a layer of an intermediate layer of a second coating material interposed between the first coating material and the substrate, the second coating material being different from the first coating material and the substrate, comprising the steps of:

directing a beam of a radiant energy onto the coated substrate, the radiant energy being capable of stimulating characteristic secondary X-rays from the first coating material, the seond coating material and the substrate material, detecting the characteristic secondary X-rays from the coating material and the substrate material, generating a signal which is indicative of the intensity of the detected secondary X-rays which are characteristic of the first coating material, generating a signal which is indicative of the intensity of the detected secondary X-rays which are characteristic of the substrate material, generating a first ratio signal which is a ratio of the two signals indicative of the secondary emission intensities of the first coating material and the substrate material, generating in response to the first ratio signal a signal which is indicative of the thickness of the layer of the first coating material, generating a signal which is indicative of the intensity of the detected secondary X-rays which are characteristic of the intermediate coating material, generating a signal which is indicative of the intensity of the detected secondary X-rays which are characteristic of the intermediate coating material and the substrate material, generating a second ratio signal which is a ratio of the two signals indicative of the secondary emission intensities of the intermediate coating material and the sum of the intermediate coating and substrate materials, and generating in response to the second ratio signal a signal which is indicative of the thickness of the intermediate layer of coating material.

6. An apparatus according to claim 1, wherein the substrate is a wire.

7. A method according to claim 5, wherein there are further included the steps of generating a second error signal in response to the intermediate layer thickness signal which is indicative of any variation of the intermediate coating thickness from a predetermined level, and varying an intermediate coating process parameter in response to the second error signal in a manner such that the intermediate coating thickness is altered in a direction which will cause the second error signal to diminish.

8. An apparatus for measuring the thickness of an intermediate layer of a coating material, the intermediate layer being deposited over a substrate material and having an outer layer of coating material deposited thereover, the material of the intermediate layer being different from the substrate and outer layer materials, the apparatus comprising a source of a radiant energy which is directed onto the coating substrate, the radiant energy being capable of stimulating characteristic secondary X-rays from the intermediate and outer coating materials and the substrate material, an X-ray analysis spectrometer located to receive the characteristic secondary X-rays from the intermediate and outer coating materials and the substrate material, the X-ray analysis spectrometer producing an output signal containing intensity information for a wide energy spectrum selected to include the characteristic secondary X-rays from the intermediate and outer coating materials and the substrate material, a coating thickness measuring circuit connected to the output of the X-ray analysis spectrometer which includes means for generating a signal which is indicative of the intensity of secondary X-rays received by the X-ray analysis spectrometer which are characteristic of the intermediate coating material, means for generating a signal which is indicative of the intensity of secondary X-rays received by the X-ray analysis spectrometer which are characteristic of the intermediate coating material and the substrate material, and means for generating a signal which is a ratio of the two signals indicative of the secondary emission intensities, and means for generating, in response to the ratio signal, a signal which is indicative of the thickness of the intermediate layer of coating material.

9. An apparatus according to claim 8, wherein there are further included means for generating an error signal in response to the thickness signal which is indicative of any variation of the intermediate coating thickness from a predetermined level, and means for varying an intermediate coating process parameter in response to the error signal in a manner such that the intermediate coating thickness is altered in a direction which will cause the error signal to diminish.

10. A method for measuring the thickness of a layer of a coating material deposited over a substrate material which is different from the coating material comprising the steps of:

directing a beam of a radiant energy onto the coated substrate, the radiant energy being capable of stimulating characteristic secondary X-rays from the coating material and the substrate material, detecting the characteristic secondary X-rays from the coating material and the substrate material, generating a coating material signal which is indicative of the intensity of the detected secondary X-rays which are characteristic of the coating material, including, separating X-ray counts of X-ray line energies associated exclusively with the coating material, and collecting the X-ray counts associated with the coating material for a preselected period of time, the timed collection of counts forming the coating material signal, generating a substrate material signal which is indicative of the intensity of the detected secondary X-rays which are characteristic of the substrate material, including, separating X-ray counts of X-ray line energies associated exclusively with the substrate material, and collecting the X-ray counts associated with the substrate material for a preselected period of time, the timed collection of counts forming the substrate material signal, generating a signal which is a ratio of the two signals indicative of the secondary emission intensities, and generating in response to the ratio signal a signal which is indicative of the thickness of the layer of coating material.

11. A method according to claim 10, wherein there is further included the step of advancing the coating substrate continually so that the thickness of the coating layer is determined continuously in real time.

12. A method according to claim 10, wherein there are further included the steps of generating an error signal in response to the thickness signal which is indicative of any variation of the coating thickness from a predetermined level, and varying a coating process parameter in response to the error signal in a manner such that the coating thickness is altered in a direction which will cause the error signal to diminish.

13. A method according to claim 12, wherein the step of generating an error signal includes the steps of supplying a reference signal indicative of the desired thickness of the coating material, and comparing the coating thickness signal with the reference signal to generate the error signal.

* * * * *

PO-1050
(5/69)

UNITED STATES PATENT OFFICE
CERTIFICATE OF CORRECTION

Patent No. 3,984,679  Dated October 5, 1976

Inventor(s) Paul Lublin and Donald Koffman

It is certified that error appears in the above-identified patent and that said Letters Patent are hereby corrected as shown below:

In the Abstract, line 16, "the", first occurrence, should read --and--;

Column 4, line 32, "$WL\lambda_1$" should read --$WL\gamma_1$--;

Column 5, line 10, "prefered" should read --preferred--;

Column 13, line 10, "seccondary" should read --secondary--.

Signed and Sealed this

Fourteenth Day of December 1976

[SEAL]

Attest:

RUTH C. MASON
Attesting Officer

C. MARSHALL DANN
Commissioner of Patents and Trademarks